United States Patent [19]

Heiman et al.

[11] Patent Number: 5,258,512
[45] Date of Patent: Nov. 2, 1993

[54] IMMUNOASSAY FOR OPIATE ALKALOIDS AND THEIR METABOLITES; TRACERS, IMMUNOGENS AND ANTIBODIES

[75] Inventors: Daniel F. Heiman, Libertyville; Daniel S. Raden, Hawthorn Woods; Robert E. Dubler, Gurnee, all of Ill.

[73] Assignee: Abbott Laboratories, Abbott Park, Ill.

[21] Appl. No.: 940,589

[22] Filed: Sep. 4, 1992

Related U.S. Application Data

[60] Division of Ser. No. 316,846, Feb. 28, 1989, which is a continuation of Ser. No. 885,054, Jul. 14, 1986, Pat. No. 5,227,981.

[51] Int. Cl.$^5$ .......................................... C07D 489/02
[52] U.S. Cl. ........................................ 546/44; 546/45; 546/46
[58] Field of Search ............................ 546/44, 45, 46

[56] References Cited

U.S. PATENT DOCUMENTS 3,966,764  6/1976  Goldstein et al. ................ 546/45
4,199,559  4/1980  Ullman et al. ................... 436/537

*Primary Examiner*—Mukund J. Shah
*Assistant Examiner*—Y. N. Gupta
*Attorney, Agent, or Firm*—Gregory W. Steele; Thomas M. Breininger

[57] ABSTRACT

The present invention is directed to a fluorescence polarization assay for opiate alkaloids and their metabolites, to the various components needed for preparing and carrying out such an assay and to methods of making these components. Specifically, tracers, immunogens and antibodies are disclosed, as well as methods for making them. The tracers and the immunogens are made from substituted opiate alkaloids. A fluorescein moiety is included in the tracers, while a poly(amino acid) forms a part of the immunogens. The assay is conducted by measuring the degree of polarization retention of the fluorescence resulting when a sample mixed with antiserum and tracer is irradiated with plane-polarized light.

2 Claims, 8 Drawing Sheets

LACTONE ⇌ ACID

IMMUNOASSAY FOR OPIATE ALKALOIDS AND THEIR METABOLITES; TRACERS, IMMUNOGENS AND ANTIBODIES

This is a division of application Ser. No. 07/316,846, filed Feb. 28, 1989, now allowed which is a continuation of application Ser. No. 885,054 filed Jul. 14, 1986 now U.S. Pat. No. 5,227,981.

BACKGROUND OF THE INVENTION

1. Technical Field

The present invention relates to a method and reagents for a fluorescence polarization immunoassay procedure for determining the presence or amount of alkaloids of the opiate class or their metabolites in fluids, especially biological fluids such as urine, serum or plasma, and to methods for making the reagents. More specifically, the invention relates to 1) reagents (tracers and antibodies) for determining the presence or amount of opiate alkaloids and/or their metabolites in a sample; 2) immunogen compounds used to raise the antibodies; 3) synthetic methods used to prepare the tracer and immunogen compounds; and 4) analytical methods for conducting the assay.

2. Background Art

Plants of the poppy family, particularly *Papaver Somniferum*, produce as a result of their secondary metabolism significant amounts of a number of pentacyclic alkaloids known as opiates. The most important ones are morphine (FIG. 1) and codeine (FIG. 2). These compounds have been employed medicinally from ancient times for their narcotic, analgesic or anesthetid properties. It has also been known from antiquity that repeated use of these compounds leads to a craving for or addiction to them which tends to progress to a level where it interferes with the normal functioning of the individual so affected.

In attempts to alter their pharmacological properties, medicinal chemists have produced a large number of semi synthetic derivatives of the naturally occurring opiates which retain the pentacyclic alkaloid skeleton, some of which are produced commercially for medicinal use. Important examples include diacetylmorphine (heroin, FIG. 3), Hydromorphone (FIG. 4), Hydrocodone (FIG. 5), Oxycodone (FIG. 6), Oxymorphone (FIG. 7) and Levorphanol (FIG. 8). These derivatives retain the addiction liability of the parent compounds to a greater or lesser degree.

Because of the problems created by abuse of the opiates, the production, distribution and use of most members of this class are rigidly controlled throughout the Western world. These efforts are supported in part by methods for detecting their unauthorized consumption which are rapid, reliable and selective for the opiates and/or their metabolites. Such testing is most frequently carried out on urine samples, since they are normally more accessible than blood samples. Other biological fluids have not been investigated extensively as media for these analyses.

In the past, opiates have been detected in biological samples by thin layer chromatography (TLC), high pressure liquid chromatography (HPLC), gas chromatography (GC), radioimmunoassay (RIA) or enzyme immunoassay (EIA). However, these assay methods are not without drawbacks. TLC is labor intensive and lacks sensitivity. Both HPLC and GC are labor intensive, requiring highly trained personnel to carry out extractions of the analyte from the biological matrix, while GC requires a derivatization step as well. RIA reagents degrade spontaneously, require burdensome methods of protecting and monitoring the safety of the personnel involved, and generate hazardous waste which must be disposed of in a secure manner. EIAs are subject to variability due to thermal and/or bacterial lability of reagents and to matrix effects which alter enzyme activity.

Fluorescence polarization immunoassay (FPIA) procedures provide a reliable quantitative means for measuring the amount of tracer antibody complex produced in a homogeneous competitive binding assay. Typically, in such a competitive binding immunoassay a ligand (a substance of biological interest to be determined by the technique) competes with a labeled reagent, or "ligand analog," or "tracer," for a limited number of receptor binding sites on antibodies specific to the ligand and ligand analog. The concentration of ligand in the sample determines the amount of ligand analog which binds to the antibody: the amount of ligand analog that will bind is inversely proportional to the concentration of ligand in the sample, because the ligand and the ligand analog each bind to the antibody in proportion to their respective concentrations.

Fluorescence polarization techniques are based on the principle that a fluorescent labeled compound, when excited by plane polarized light, will emit fluorescence having a degree of polarization inversely related to its rate of rotation. Accordingly, when a tracer-antibody complex having a fluorescent label is excited with plane polarized light, the emitted light remains highly polarized because the fluorophore is constrained from rotating between the time that light is absorbed and emitted. In contrast, when an unbound tracer is excited by plane-polarized light, its rotation is much faster than that of the corresponding tracer-antibody conjugate. As a result, the light emitted from the unbound tracer molecules is depolarized.

Such fluorescence polarization techniques have been applied in U.S. Pat. No. 4,420,568 to Wang, et al., which is directed to the use of a triazinylamino fluorescin moiety as the fluorophore.

Opiate antigen conjugates and antibodies have been described in U.S. Pat. No. 3,709,868 to Spector, in U.S. Pat. No. 3,867,366 to Rubenstein and Ullman, in U.S. Pat. No. 4,022,878 to Gross, in Science 176, 1143 (1972) and Science 178, 647 (1972) by Wainer, et al., in Japanese Journal of Pharmacology 24, 165 (1974) and op. cit. 24, 707 (1974) by Koida, et al., in Proceedings of the Society for Endocrinology 64, 6P (1975) by Morris, et al., in Research Communications in Chemical Pathology and Pharmacology 29, 535 (1980) and op. cit. 32, 545 (1981) by Dixon, et al., in Journal of Pharmaceutical Sciences 69, 160 (1980) by Pittman, et., in European Journal of Clinical Pharmacology 18, 339 (1980) by Bartlett, et al., and in Clinical Chemistry 27, 1524 (1981) by Findlay, et al. Fluorescein conjugates of opiates have been described in U.S. Pat. Nos. 3,998,943 and 4,255,329 to Ullman, in U.S. Pat. No. 3,935,074 to Rubenstein and Leute, in the Journal of Biological Chemistry 251, 4172 (1976) by Ullman et al. and in Life Sciences 33 Sup. I, 423 (1983) by Kolb et al.

The present invention offers an advance in the art beyond that described supra, particularly in that effective immunogens, selective antibodies, highly sensitive fluorescent tracers, methods for preparing the antibodies and fluorescent tracers, and an assay employing the tracers and antibodies are provided specifically for the determination of one or more opiate alkaloids in a sample. An assay conducted in accordance with the present invention is particularly accurate, as will be explained infra.

SUMMARY OF THE INVENTION

This invention is directed to haptens and immunogens used to raise antibodies which can be employed in an assay for opiate alkaloids or their metabolites, to tracers for use in fluorescence polarization immunoassays for opiate alkaloids or their metabolites, to methods for conducting such assays and to methods for synthesizing the tracers, haptens and immunogens.

Accordingly, a first aspect of the invention relates to the discovery of novel compounds which, when covalently attached to an immunogenic carrier substance such as a protein and used to raise antibodies, provide antisera with high cross-reactivities for a number of different opiate alkaloids and their metabolites, while showing little affinity for other alkaloids or drugs. Thus, according to the first aspect of the present invention, there are provided compounds which are dialdehydes resulting from mild oxidative ring opening of the glucuronide metabolic conjugate at the 3-position of an opiate alkaloid, represented by the structural formula shown in FIG. 9 of the drawings, wherein one of $\alpha$ and $\alpha'$ is hydrogen and the other is hydroxyl, or both are taken together to form $=O$ (ketone); $\beta$ and $\beta'$ are both hydrogen, or both are taken together to form a bond joining the carbon atoms to which they are attached; and $\alpha''$ is hydrogen or hydroxyl.

According to a second aspect of the invention, a method is provided for making an immunogen comprising the steps of oxidizing a glucuronide conjugate of an opiate alkaloid, represented by the structural formula shown in FIG. 10 of the drawings, wherein $\alpha$, $\alpha'$ $\alpha''$, $\beta$ and $\beta'$ are defined as supra, with water soluble periodate, allowing the aldehyde compound so formed to react with primary alkyl amino groups on an immunogenic carrier substance such as a protein, and reducing the resulting condensation product with a borohydride reagent such as sodium borohydride or sodium cyanoborohydride.

A third aspect of the invention relates to antibodies raised by the novel immunogen. According to this aspect, antibodies are prepared in response to a compound synthesized as described supra, by methods well known to those skilled in the art.

A fourth aspect of the inventions relates to the discovery of unique tracers having novel structures. According to this aspect of the invention, these tracers can be represented by the general structural formula shown in FIG. 11 of the drawings wherein:

one of X and Y is hydrogen and the other is hydrogen, fluorine, chlorine, bromine, cyano or lower alkyl (one to three carbon atoms);

Z is $>NH$, $>C=O$, $>C=NH$ or $>SO_2$;

Q is fluorescein or a fluorescein derivative;

R is a linking group consisting of from 0 to 20 carbon atoms and nonmetallic heteroatoms, including not more than 12 heteroatoms, arranged in a straight or branched chain and containing up to two ring structures, with the proviso that not more than four of said heteroatoms may be linked in sequence, nor may more than two sulfur or two nitrogen or one oxygen atom be linked in sequence;

E is an electron pair, an oxygen atom or methyl;

$\alpha$ and $\alpha'$ are both hydrogen or one of them is hydrogen while the other is hydroxyl, methyl or fluoro, or both are taken together to form $=O$ (ketone);

$\alpha''$ is hydrogen or hydroxyl; and $\beta$ and $\beta'$ are both hydrogen, or both are taken together to form a bond joining the two carbon atoms to which they are attached, with the proviso that $\beta$ and $\beta'$ do not form a bond when $\alpha$ is H, $\alpha'$ is OH, E is a nonbonding electron pair and $\alpha''$, X and Y are all hydrogen.

A fifth aspect of the invention relates to the discovery of unique compounds which serve as synthetic precursors to the tracer compounds described supra. According to this aspect of the invention the tracer precursors can be represented by the structural formula shown in FIG. 11 of the drawings wherein:

one of X and Y is hydrogen and the other is hydrogen, fluorine, chlorine, bromine, cyano or lower alkyl (one to three carbon atoms);

Z is a linking functional group such as $>NH$, $C=O$, $>SO_2$ or $—S—$;

Q is hydrogen, hydroxyl or a leaving group. [For purposes of this disclosure, a "leaving group" is a halogen, an acyloxy group (including a carbonate ester), a succinimidyloxyl or phthalimidyloxy group, an alkoxy or phenoxy or substituted phenoxy group, an imidazolyl group, a benzotriazolyloxy group or any of the other similar activating groups well known to those skilled in the art;]

R is a linking group consisting of from 0 to 20 carbon atoms and heteroatoms, including not more than 12 heteroatoms, arranged in a straight or branched chain and containing up to two ring structures, with the proviso that not more than four heteroatoms may be linked in sequence, nor may more than two sulfur or two nitrogen or one oxygen atom be linked in sequence;

E is a nonbonding electron pair, an oxygen atom or methyl;

$\alpha$ and $\alpha'$ are both hydrogen, or one of them is hydrogen while the other is hydroxyl, methyl or fluoro, or both are taken together to form $=O$ (ketone);

$\alpha''$ is hydrogen or hydroxyl; and $\beta$ and $\beta'$ are both hydrogen, or both are taken together to form a bond joining the two carbon atoms to which they are attached, with the proviso that $\beta$ and $\beta'$ do not form a bond when $\alpha$ is H, $\alpha'$ is OH, E is an electron pair and $\alpha''$, X and Y are all hydrogen.

According to a sixth aspect of the invention, a method is provided for making a tracer by coupling a compound represented by the structural formula shown in FIG. 11, wherein:

one of X and Y is hydrogen and the other is hydrogen, fluorine, chlorine, bromine, cyano or lower alkyl (one to three carbon atoms);

Z is a linking functional group such as $>NH$, $>C=O$, $>SO_2$ or $—S—$;

Q is hydrogen, hydroxyl or a leaving group;

R is a linking group consisting of from 0 to 20 carbon atoms and heteroatoms, including not more than 12 heteroatoms, arranged in a straight or branched chain and containing up to two ring structures, with the proviso that not more than four heteroatoms may be linked in sequence, nor may more than two sulfur or two nitrogen or one oxygen atom be linked in sequence;

E is a nonbonding electron pair, an oxygen atom or methyl;

$\alpha$ and $\alpha'$ are both hydrogen, or one of them is hydrogen while the other is hydroxyl, methyl or fluoro, or both are taken together to form $=O$ (ketone);

$\alpha''$ is hydrogen or hydroxyl; and $\beta$ and $\beta'$ are both hydrogen, or both are taken together to form a bond joining the two carbon atoms to which they are attached, with the proviso that $\beta$ and $\beta'$ do not form a bond when $\alpha$ is H, $\alpha'$ is OH, E is an electron pair and $\alpha''$, X and Y are all hydrogen;

with fluorescein or a derivative of fluorescein.

A seventh aspect of the invention relates to an analytical method, i.e., a method for conducting an assay employing as reagents the tracers of FIG. 11, wherein Q is fluorescein or a fluorescein derivative, and antisera to opiate alkaloids raised in response t immunogens prepared as described supra. According to this seventh aspect of the invention, an improved fluorescence polarization immunoassay is provided, comprising the steps of contacting a fluid suspected of containing opiate alkaloid(s) or metabolite(s) therefrom with antisera to opiate alkaloid(s) and a fluorescein-labelled opiate derivative (i.e., a compound represented by FIG. 11, with the proviso that the substitution pattern of the tracer as defined by the variables $\alpha$, $\alpha'$, $\alpha''$, $\beta$, $\beta'$, E, X and Y is different from that of the immunogen employed in raising the antiserum) capable of producing a detectable fluorescence polarization response to the presence of the antiserum in a homogeneous solution, while passing plane-polarized light through the homogeneous solution, and measuring the fluorescence polarization response therefrom.

An eighth aspect of the invention relates to the elimination of potential fluorescence interference by riboflavin. Riboflavin binding protein (RBP) is added either directly to each sample or to one or more of the reagents utilized in the assay, wherein it binds all riboflavin present into RBP-riboflavin complexes, thus eliminating fluorescence interference. Other fluorescence quenching substances may also be utilized for this purpose.

BRIEF DESCRIPTION OF THE DRAWINGS

In the following figures the symbol "F1" represents a fluorescein moiety, and the various other symbols are noted in the Detailed Description. Note that $\alpha$ and $\alpha''$ are intended to be attached on the near face of the molecule represented and $\alpha'$ is to be attached to the far face of the molecule.

FIG. 11 represents a precursor for the tracers.

DETAILED DESCRIPTION OF THE INVENTION

Figure 1:
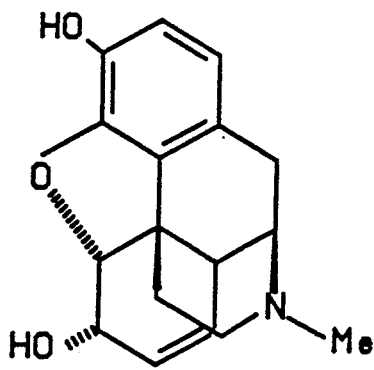
FIGS. 1 through 8 show the structures of various important members of the class of opiate alkaloids to be detected or determined in accordance with the present invention.

The various aspects of the invention will now be discussed in detail in relation to the Figures.

Definitions and Explanatory Material

The present invention involves the use of fluorescein and derivatives of fluorescein. In particular, a necessary property of fluorescein and its derivatives for the usefulness of the tracer compounds is the fluorescence of fluorescein. Fluorescein exists in two tautomeric forms, illustrated in FIG. 12, depending on the acid concentration (pH) of the environment. In the open (acid) form, there are a number of conjugated double bonds which make that form of fluorescein (and compounds containing a fluorescein moiety) capable of absorbing blue light and emitting green fluorescence after an excited state lifetime of about four nanoseconds. When the open and closed forms coexist, the relative concentration of molecules in the open and closed forms is easily altered by adjustment of the pH level. Generally, the tracer compounds of the present invention exist in solution as biologically acceptable salts such as sodium, potassium, ammonium and the like, allowing the compounds to exist in their open, fluorescent form when employed in the analytical methods of the present invention. The specific salt present will depend on the buffer employed to adjust the pH level. For example, in the presence of a sodium phosphate buffer, the compounds in the present invention will generally exist in the open form, as a sodium salt.

As used herein, the term "fluorescein", either as an individual compound or as a component of a larger compound, is meant to include both the open and closed forms, if they exist for a particular molecule, except in the context of fluorescence. An open form is necessary for the fluorescence to occur.

The numbering of carbon atoms of the fluorescein molecule varies, depending upon whether the open or closed form of the molecule is considered. Accordingly, the literature concerning fluorescein and its compounds is not uniform as to carbon atom numbering. In the closed form, the para carbon to the carbonyl of the lactone on the phenyl ring is numbered "6". In the open form, the para-carbon to the carboxylic acid group on the phenyl ring is numbered "5" (see FIG. 3). In this disclosure the numbering of the closed form is adopted because the raw materials used in the syntheses are most popularly numbered with that system. The carbon atom of fluorescein and its compounds which is opposite the carboxyl group is therefore numbered "6" for the purposes of the present disclosure.

A tracer in solution which is not complexed to an antibody is free to rotate in less than the time required for absorption and re emission of fluorescent light. As a result, the re-emitted light is relatively randomly oriented so that the fluorescence polarization of a tracer not complexed to an antibody is low, approaching zero. Upon complexing with a specific antibody, the tracer antibody complex thus formed assumes the rotation of the antibody molecule, which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertically polarized component of the emitted light, the polarization of fluorescence in the reaction mixture may be accurately determined. The precise relationship between polarization and concentration of the ligand to be determined may conveniently be established by measuring the polarization values of calibrators with known concentrations. The concentration of the ligand can be interpolated from a standard curve prepared in this manner.

The particular antibodies and tracers formed in accordance with this invention have been found to produce very good assays, as discussed infra.

The Reagents

The objective in designing a competitive binding immunoassay for opiate alkaloids and their metabolites is to set up a reasonably balanced competition between the drug (that is, the opiate alkaloid or metabolite therefrom) and the tracer for the recognition sites on the antibody. Widely varying structures for haptens and tracers may be successful in achieving this goal. For the purpose of this invention, "haptens" are precursors of the immunogens, comprising generally a glucuronic acid conjugate of an opiate alkaloid.

The Structure of the Immunogens

Usable antibodies can be produced from a variety of opiate alkaloid derivatives. Immunogens prepared from a given opiate such as morphine glucuronide elicit antibodies which show very high affinity for that drug, but which may also show affinity for other opiates having the same basic pentacyclic alkaloid structure. Proper selection of antisera may provide either very narrow or very broad selectivity of response.

Figure 9:
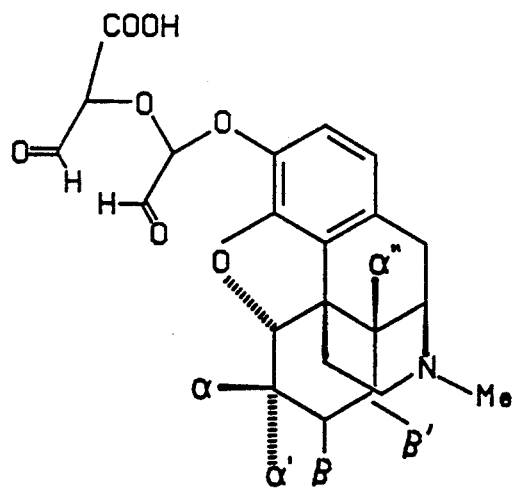
FIG. 9 shows a general structural formula for the haptens or precursors for the immunogens of the present invention.

In the presently preferred form of the invention, the immunogens are derived from morphine glucuronide, the compound having the formula shown in FIG. 9, wherein $\alpha$ is hydrogen, $\alpha'$ is hydroxyl, $\alpha''$ is hydrogen and $\beta$ and $\beta'$ form a bond. This structure is preferred for use in a screening assay for opiate alkaloid abuse because morphine and its metabolic precursor diacetylmorphine (heroin) are the compounds most frequently abused. Thus, the antibodies produced in response to the preferred precursor described supra are those which best recognize morphine and morphine glucuronide, the two compounds most likely to be encountered in biological fluids obtained from persons suspected of opiate abuse.

Although thyroglobulin is the immunogenic carrier substance employed in the synthetic examples set out infra, it should be understood that various protein carriers can be employed, including albumins, serum proteins, e.g., globulins, ocular lens proteins, lipoproteins and the like. Illustrative protein carriers include bovine serum albumin, keyhole limpet hemocyanin, egg ovalbumin, bovine gamma globulin, etc. Alternatively, synthetic poly(amino acids) having a sufficient number of available amino groups (e.g., those on lysine or ornithine residues) can be employed, as can many other synthetic or natural polymeric materials bearing reactive functional groups. In addition, carbohydrates, yeasts, polysaccharides or any other substance that can be used as an immunological carrier can be conjugated to the hapten to produce an immunogen.

The Antibodies

The antibodies employed in the present invention are prepared by eliciting a response in rabbits or sheep to appropriate immunogens. The immunogen is administered to animals or to in vitro cultures of immunocompetent cells by a series of inoculations, in a manner well known to those skilled in the art. It should be understood that although sheep were the preferred immune host to opiate alkaloid immunogens in the experiments detailed herein, any in vivo or in vitro host capable of producing antibodies may be employed.

The Structure of the Tracers

Figure 11:
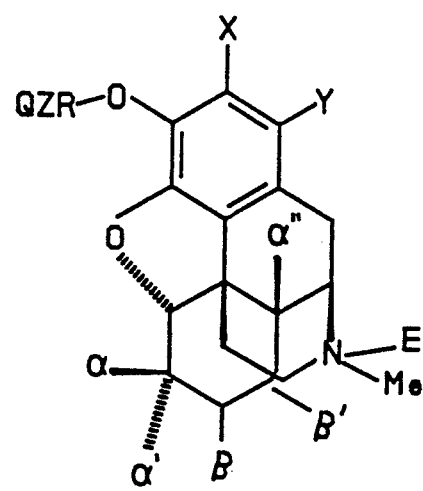
FIG. 11 shows a general structural formula for the tracers of the present invention, as well as the classes of reactants used in preparing them.

The tracers of the present invention can be represented by the general structural formula shown in FIG. 11. In a preferred form of the invention, the tracer has the structural formula shown in FIG. 14.

Figures 1, 13:
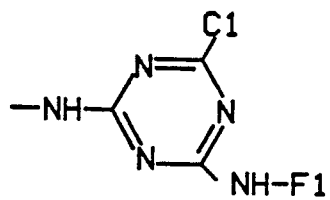
FIG. 13 shows various linkages that couple the fluorescein moiety to the precursor in FIG. 11, when
Figures 2, 13:
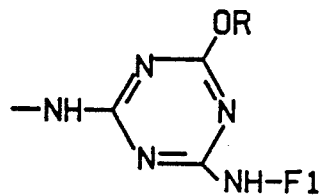
Figures 3, 13:
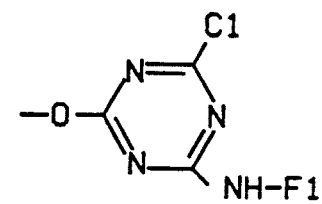
Figures 4, 13:
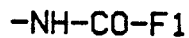
Figures 5, 13:
Figures 6, 13:
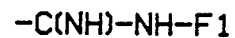
Figures 7, 13:
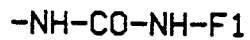
Figures 8, 13:
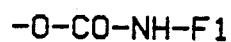
Figures 9, 13:
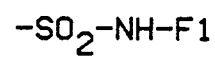
Figures 10, 13:
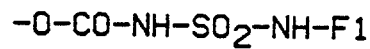

The tracer is an opiate alkaloid derivative that is linked to a fluorescein derivative by, for example, an amide, an amidine, a urea, a carbamate, a sulfonamide, a triazinylamino, or a sulfonylcarbamate group, as shown in FIG. 13. The tracers are prepared by linking the appropriate fluorescein derivative to an opiate alkaloid derivative containing an amino, carboxylic acid, sulfonic acid, hydroxy, imidate, hydrazide, isocyanate, chloroformate, chlorosulfonylcarbamoyl, or like group, as will be discussed in he context of the synthetic method and the Examples below.

By way of example, any of the following fluorescein derivatives can be used:

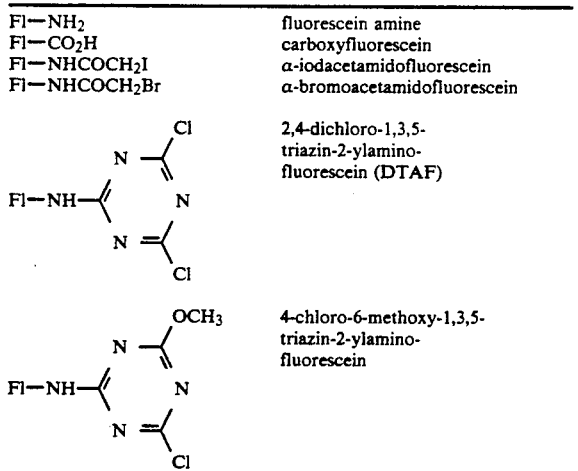

| | |
|---|---|
| Fl—NH$_2$ | fluorescein amine |
| Fl—CO$_2$H | carboxyfluorescein |
| Fl—NHCOCH$_2$I | α-iodacetamidofluorescein |
| Fl—NHCOCH$_2$Br | α-bromoacetamidofluorescein |
| | 2,4-dichloro-1,3,5-triazin-2-ylamino-fluorescein (DTAF) |
| | 4-chloro-6-methoxy-1,3,5-triazin-2-ylamino-fluorescein |

The Synthesis of the Tracers

The tracers of the present invention are made by coupling a fluorescein moiety or a derivative of fluorescein to the general structure shown in FIG. 11 wherein Q is hydrogen, hydroxyl or a leaving group; Z is NH, S, O, C=O, SO$_2$ or C=NH, and R is a linking group as defined supra. The fluorescein moiety can be linked to the amino, carboxyl, imidate or alkoxy functional group by an amide, an amidine, a urea, a carbamate, a sulfonamide, a triazinylamino or a sulfonylcarbamate linkage, as shown in FIG. 13. In the presently preferred embodiment, the fluorescein derivative is dichlorotriazinylaminofluorescein (DTAF) (isomer II), and this is coupled to a precursor shown in FIG. 11, wherein R is $CH_2C(O)NH(CH_2)_2$, Z is NH, Q is H, $\alpha$ and $\alpha''$ are H, $\alpha'$ is OH, $\beta$ and $\beta'$ are H, and E is an electron pair.

The DTAF is coupled to the aminoalkyl derivative of opiate alkaloid by stirring the two compounds in methanol at a temperature between about 0° C. and the boiling point of the solvent. Basic compounds such as triethylamine may be added if desired, especially if a salt (such as the hydrochloride or acetate) of the amine precursor is employed in the reaction. Other solvents, such as dimethylformamide or dimethylsulfoxide, may be used. Usable tracers can be prepared from a variety of opiate alkaloid derivatives.

All opiate alkaloid derivatives that have a terminal amino group, such as amino, hydrazinyl, hydrazido or the like, are coupled to carboxyfluorescein by the active ester method or the mixed anhydride method and coupled to the DTAF or alkoxy chlorotriazinylaminofluorescein simply by mixing the two materials in solution. The amino group can be converted to the isocyanate group by reaction with phosgene. This is then condensed with aminofluorescein to produce the tracer.

Opiate alkaloid derivatives having a terminal mercapto group are coupled in an inert solvent with $\alpha$-bromoacetamidofluorescein or $\alpha$-iodoacetamidofluorescein.

All opiate alkaloid derivatives that have a terminal carboxylic acid group, such as carboxylic acid, (aminohydroxy)alkylcarboxylic acid or the like, are coupled to aminofluorescein by the active ester method or mixed anhydride method.

All opiate alkaloid derivatives that have a terminal hydroxy group can be coupled to fluorescein by reaction with DTAF, $\alpha$-iodoacetamidofluorescein or $\alpha$-bromoacetamidofluorescein in solution. The hydroxy group can be converted to the chlorosulfonylcarbamoyl or chloroformate groups by reaction with chlorosulfonylisocyanate or phosgene, respectively. These derivatives are then coupled to aminofluorescein in solution to produce the tracer.

Sulfonic acid derivatives of opiate alkaloid are converted to the corresponding sulfonyl chlorides by reaction with a chlorinating reagent such as thionyl chloride, phosphoryl chloride, phosphorus pentachloride, or the like. The sulfonyl halides are then reacted with aminofluoresceins or other fluorescein derivatives bearing reactive amino groups, usually in the presence of an added basic compound, to give the tracers.

Opiate alkaloid derivatives that have a terminal nitrile group are converted to imidates in anhydrous alcohol in the presence of hydrogen chloride gas. The imidate is then coupled to fluorescein amine in solution to prepare the tracer.

The Assay

The particular tracers of the present invention have been found to detect the presence of opiate alkaloids with high sensitivity and specificity in urine samples. FIGS. 1 through 8 show the structures of the opiate alkaloid drugs that can be qualitatively detected in accordance with the present invention. The assay of the present invention provides a more rapid and convenient assay method for opiate alkaloids than prior art methods, because it requires no specimen treatment before analysis, the reagents are chemically and thermally stable, the assay system has minimal cross-reactivity to opiate-like compounds and, because of its simplicity, the assay may be carried out rapidly on highly automated equipment.

In accordance with the analytical methods of the present invention, i.e., the methods of detecting opiate alkaloids by a fluorescence immunoassay procedure using the tracer and antibody compounds of the invention, a sample containing or suspected of containing an opiate alkaloid or metabolite is intermixed with a biologically acceptable salt of a tracer and an antibody specific to opiate alkaloid and to the tracer. The opiate drug or metabolite and tracer compete for a limited number of antibody sites, resulting in the formation of complexes. Because the concentration of tracer and antibody is maintained constant, the ratio of opiate alkaloid-antibody complex to tracer-antibody complex formed is directly proportional to the amount of opiate alkaloid in the sample. Therefore, upon exciting the mixture with linearly polarized light and measuring the polarization of the fluorescence emitted by a tracer and a tracer-antibody complex, one is able to determine qualitatively whether or not opiate(s) are present in the sample.

The results can be quantified in terms of net millipolarization units, span (in millipolarization units) and relative intensity. The measurement of millipolarization units indicates the maximum polarization when a maximum amount of the tracer is bound to the antibody in the absence of any opiate alkaloid. The higher the net millipolarization units, the better the binding of the tracer to the antibody. The span is an indication of the difference between the net millipolarization at the points of maximum and minimum amount of tracer bound to the antibody. A larger span provides for a better numerical analysis of data. The intensity is a measure of the strength of the signal above background. Thus, a higher intensity will give a more accurate measurement. The intensity is determined at about 0.5 to 2.0 nanomolar for the preferred tracers of the invention, as the sum of the vertically polarized intensity plus twice the horizontally polarized intensity. The intensity of the tracer signal can range from about four times to about fifty times the background noise, depending upon the concentration of the tracer and other assay variables. For the purposes of the present invention, an intensity of at least six times that of background noise is preferred.

Figure 14:
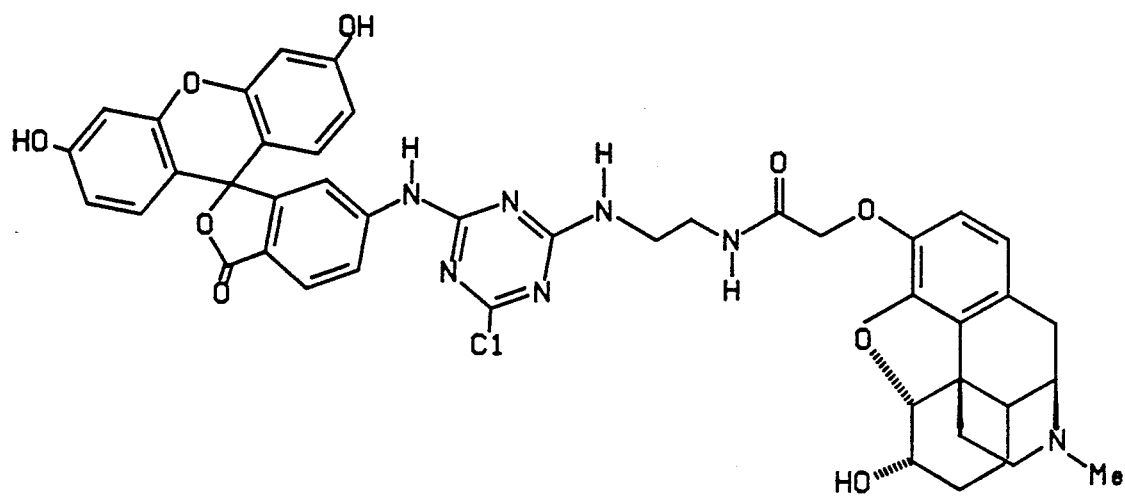
FIGS. 14 and 16 through 24 show various examples of structures of tracers in accordance with the present invention.
Figure 15:
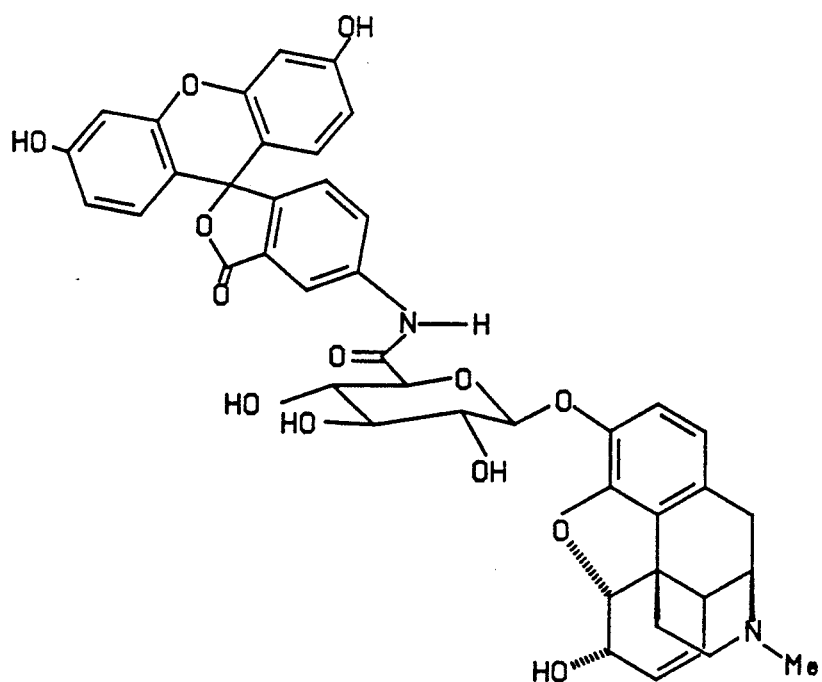
Figure 16:
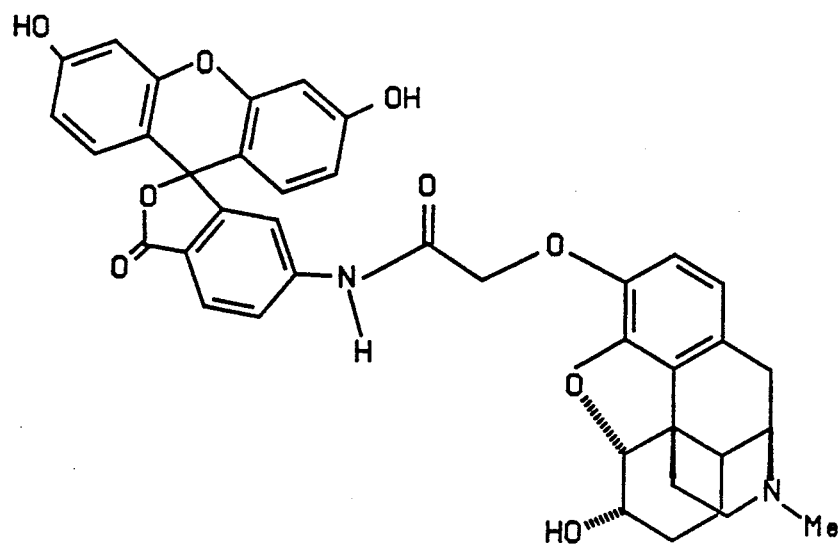
Figure 17:
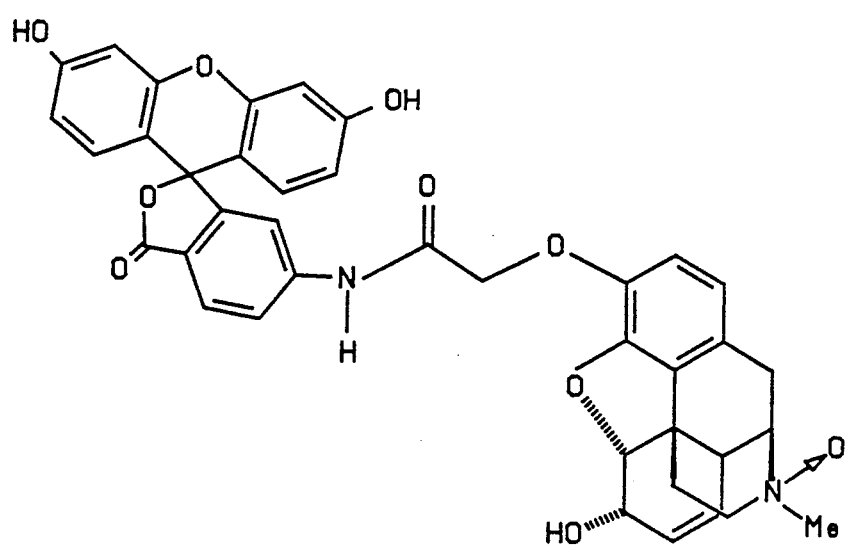
Figure 18:
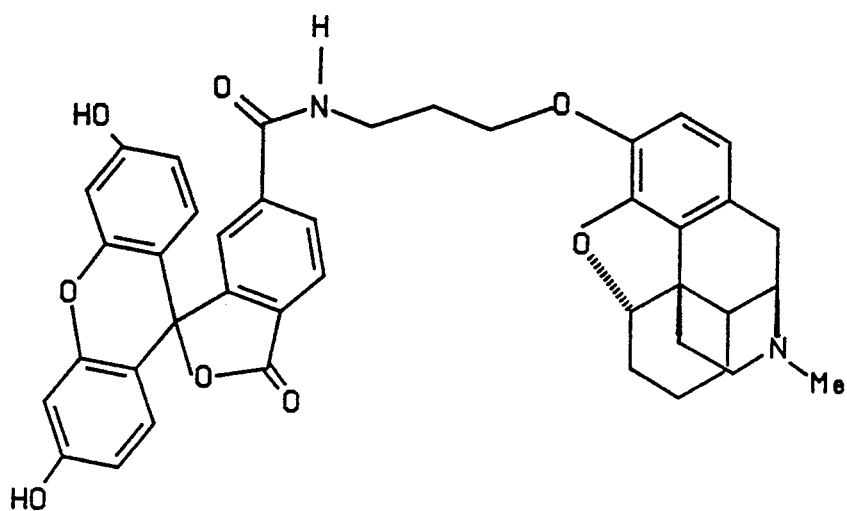
Figure 19:
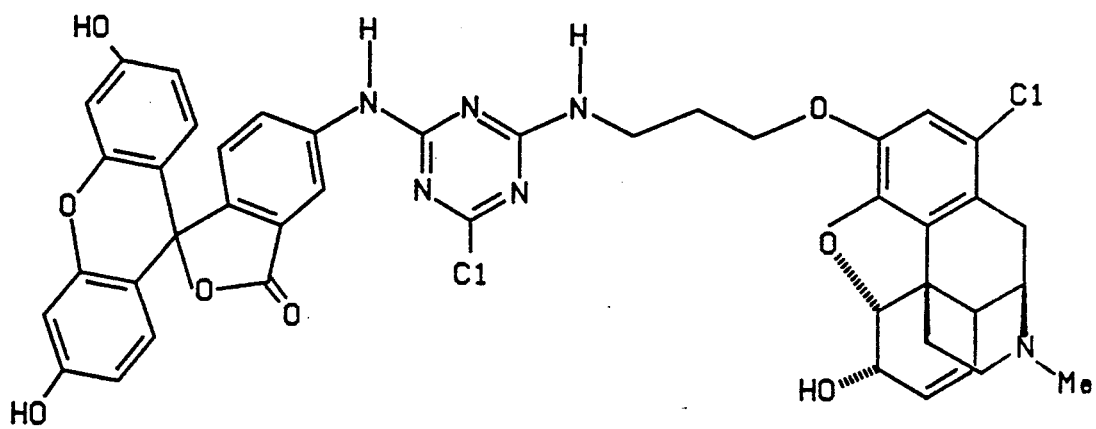
Figure 20:
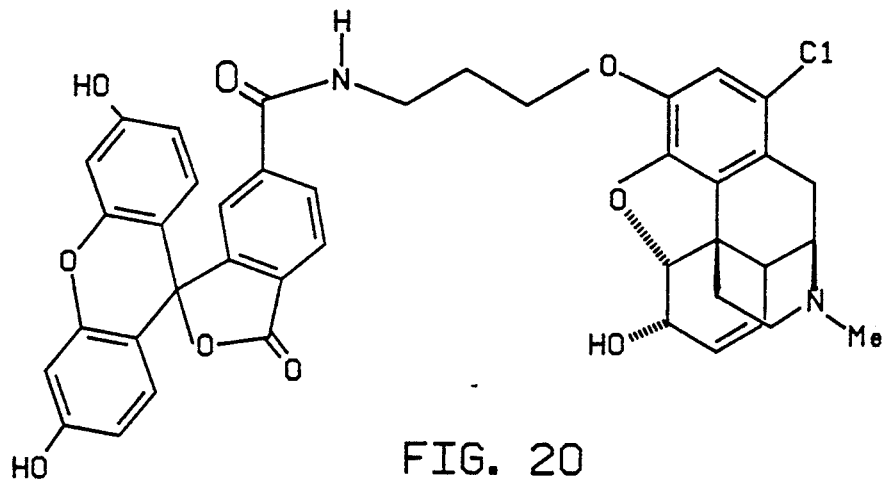
Figure 21:
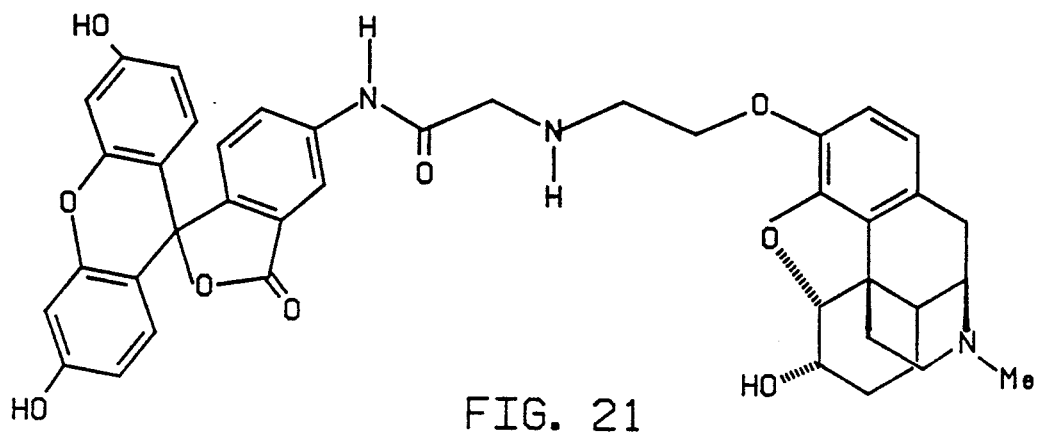
Figure 22:
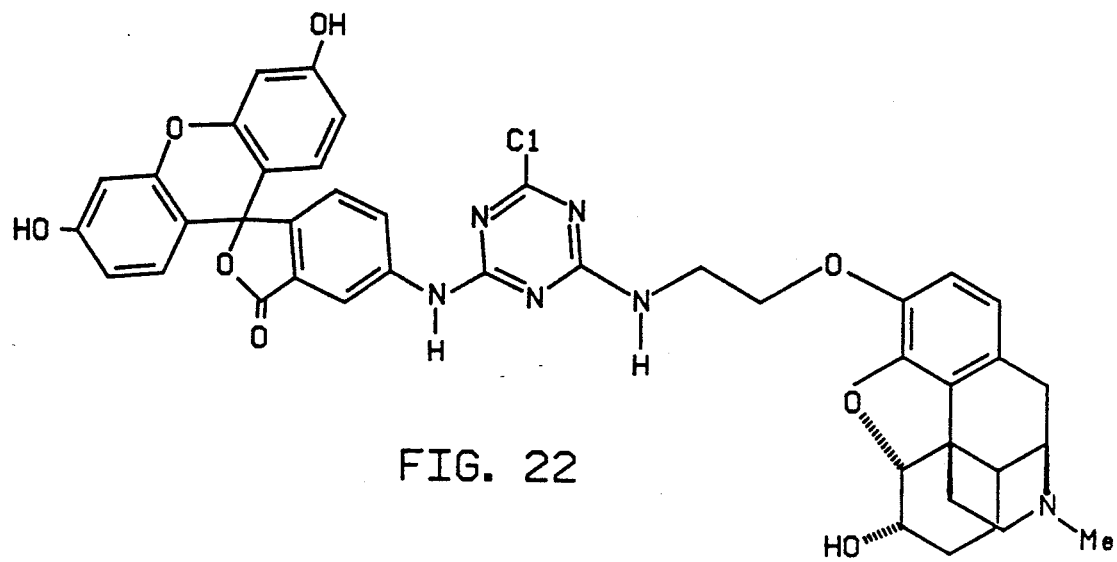
Figure 23:
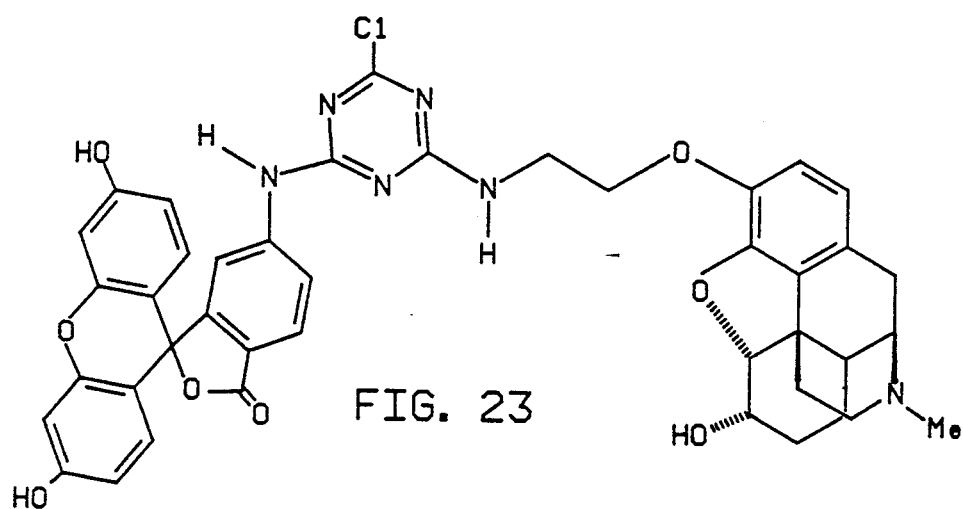
Figure 24:
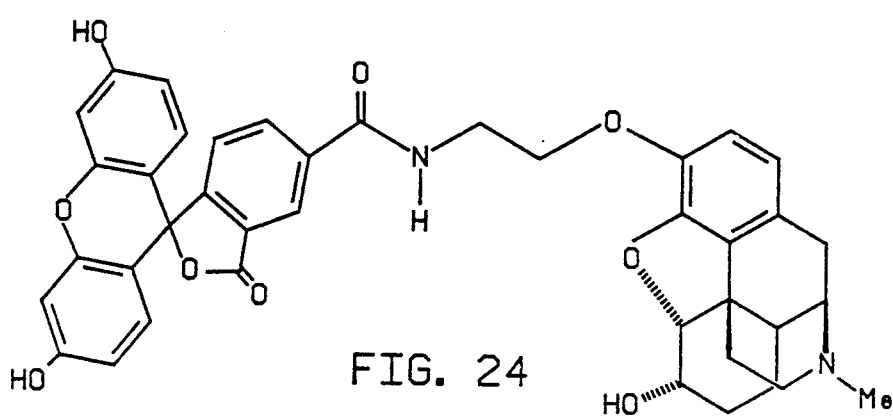
Figure 1:
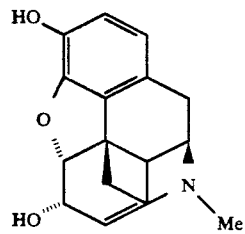
Figure 2:
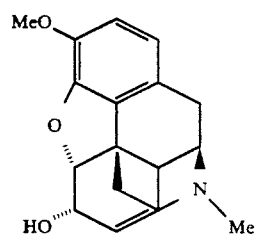
Figure 3:
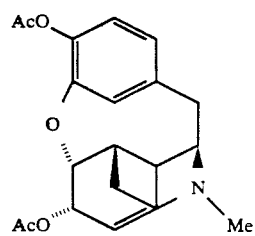
Figure 4:
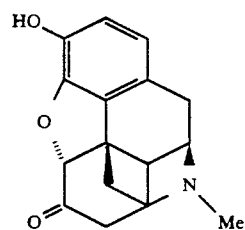
Figure 5:
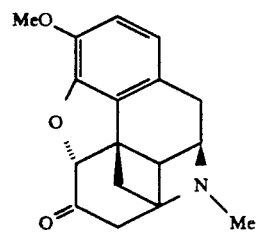
Figure 6:
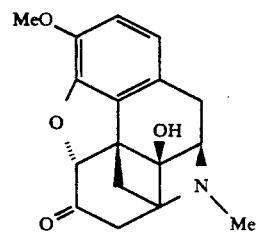
Figure 7:
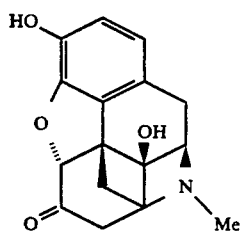
Figure 8:
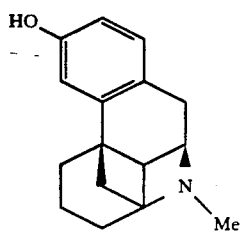
Figure 9:
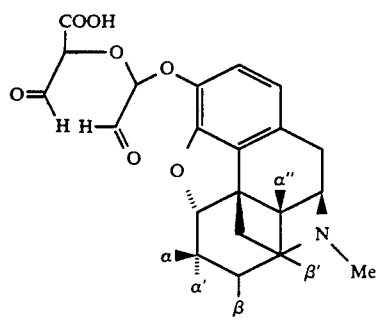
Figure 10:
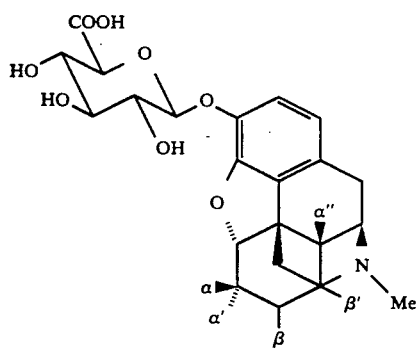
Figure 11:
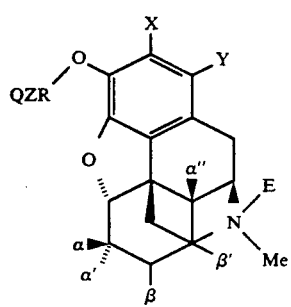
Figure 15:
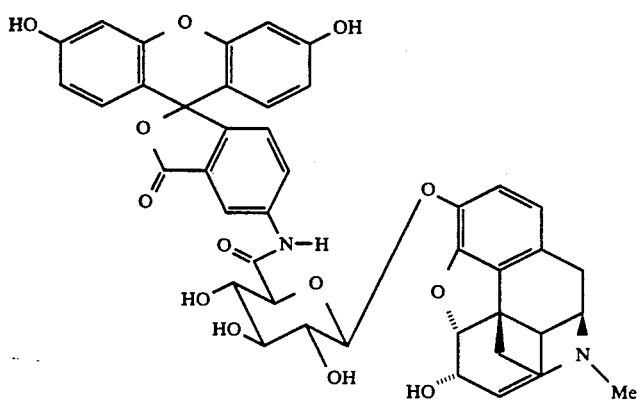
Figure 16:
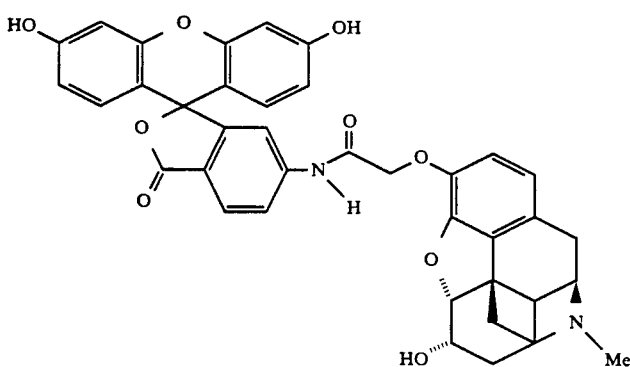
Figure 17:
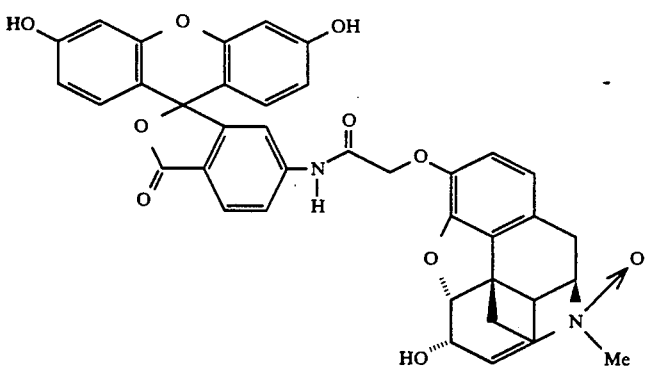
Figure 18:
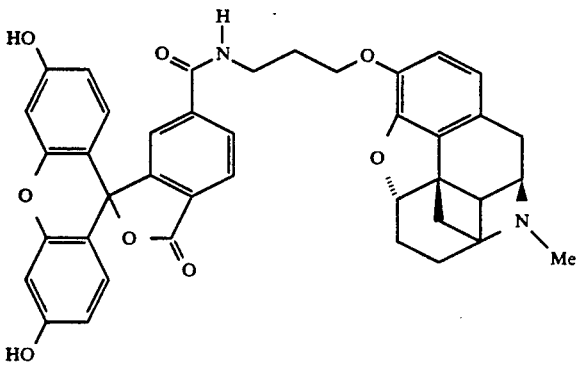
Figure 19:
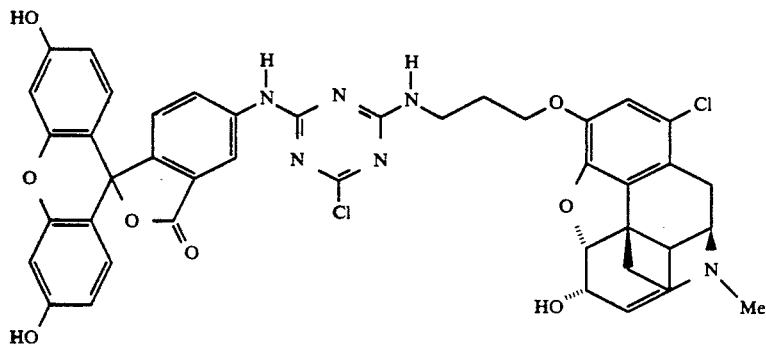
Figure 20:
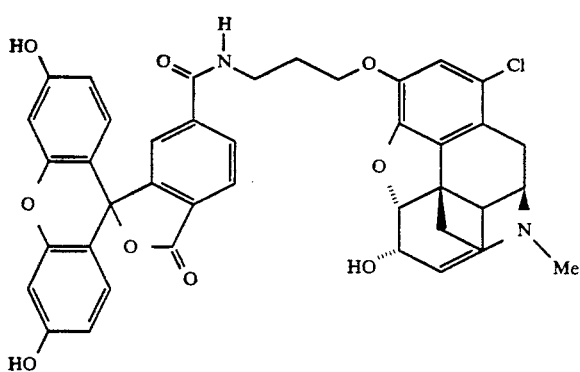
Figure 21:
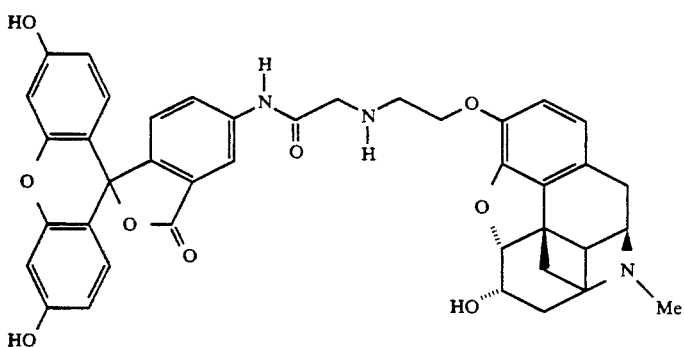
Figure 22:
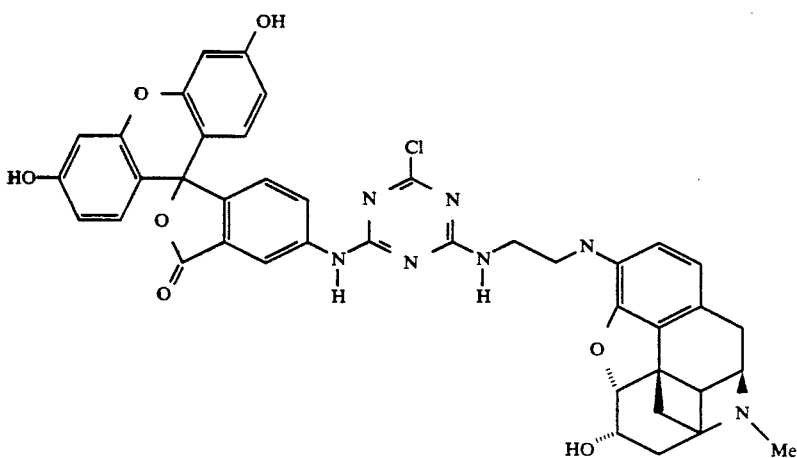

Tables I–IV shows the results obtained with various embodiments of the present invention, in terms of span, millipolarization units and intensity. In all of Tables I–III, the antiserum employed was raised in sheep; in Table IV antiserum was from rabbit. As can be seen from this data, an assay produced by use of the tracer of FIG. 14 provides excellent results and is presently the most preferred. In addition, the tracers represented by FIGS. 22, 16, and 19 also produced acceptable results and thus are alternative preferred tracers.

TABLE I

| | Sheep 104 | | | |
|---|---|---|---|---|
| Tracer | Net Polarization[a] | Cut-off Span[a,b] | Assay Span[a,c] | Intensity[d] |
| FIG. #14 | 154 | 66 | 83 | 7.0 |
| FIG. #15 | 99 | 17 | 31 | 53.1 |
| FIG. #16 | 126 | 43 | 62 | 6.8 |
| FIG. #17 | 113 | 43 | 63 | 13.9 |
| FIG. #18 | 114 | 35 | 47 | 6.8 |
| FIG. #19 | 123 | 45 | 61 | 8.4 |
| FIG. #20 | 126 | 39 | 58 | 11.9 |

TABLE I-continued

Sheep 104

| Tracer | Net Polarization[a] | Cut-off Span[a,b] | Assay Span[a,c] | Intensity[d] |
|---|---|---|---|---|
| FIG. #21 | 71 | 25 | 34 | 11.5 |
| FIG. #22 | 106 | 44 | 57 | 11.2 |
| FIG. #23 | 94 | 31 | 39 | 9.7 |
| FIG. #24 | 81 | 23 | 36 | 10.3 |

[a]Expressed in millipolarization units.
[b]Difference in polarization between a sample containing no opiate and one containing 300 ng/mL of morphine.
[c]Difference in polarization between a sample containing no opiate and one containing 1000 ng/mL of morphine.
[d]Expressed as the ratio of tracer intensity to that of background noise fluorescence.

TABLE II

Sheep 105

| Tracer | Net Polarization | Cut-off Span | Assay Span | Intensity |
|---|---|---|---|---|
| FIG. #14 | 162 | 59 | 84 | 7.0 |
| FIG. #15 | 99 | 15 | 31 | 53.1 |
| FIG. #16 | 122 | 45 | 61 | 6.8 |
| FIG. #17 | 87 | 32 | 39 | 13.9 |
| FIG. #18 | 122 | 37 | 52 | 6.8 |
| FIG. #19 | 121 | 37 | 54 | 8.4 |
| FIG. #20 | 113 | 30 | 43 | 11.9 |
| FIG. #21 | 77 | 28 | 38 | 11.5 |
| FIG. #22 | 116 | 47 | 62 | 12.2 |
| FIG. #23 | 94 | 32 | 41 | 9.7 |
| FIG. #24 | 93 | 27 | 44 | 10.3 |

TABLE III

Sheep 106

| Tracer | Net Polarization | Cut off Span | Assay Span | Intensity |
|---|---|---|---|---|
| FIG. #14 | 153 | 66 | 81 | 7.0 |
| FIG. #15 | 105 | 23 | 41 | 53.1 |
| FIG. #16 | 122 | 46 | 62 | 6.8 |
| FIG. #17 | 80 | 31 | 43 | 13.9 |
| FIG. #18 | 124 | 40 | 56 | 6.8 |
| FIG. #19 | 137 | 54 | 74 | 8.4 |
| FIG. #20 | 99 | 28 | 40 | 11.9 |
| FIG. #21 | 65 | 21 | 28 | 11.5 |
| FIG. #22 | 100 | 49 | 61 | 11.2 |
| FIG. #23 | 92 | 30 | 39 | 9.7 |
| FIG. #24 | 77 | 21 | 33 | 10.3 |

TABLE IV

Rabbit Pool

| Tracer | Net Polarization | Cut-off Span | Assay Span | Intensity |
|---|---|---|---|---|
| FIG. #14 | 160 | 74 | 87 | 7.0 |
| FIG. #15 | 149 | 38 | 66 | 53.1 |
| FIG. #16 | 137 | 58 | 76 | 6.8 |
| FIG. #17 | 108 | 51 | 67 | 13.9 |
| FIG. #18 | 143 | 53 | 76 | 6.8 |
| FIG. #19 | 118 | 49 | 62 | 8.4 |
| FIG. #20 | 107 | 34 | 49 | 11.9 |

The pH at which the method of the present invention is practiced must be sufficient to allow the fluorescein moiety of the tracers to exist in their open form. The pH may range from about 3 to 12, more preferably in the range of from about 5 to 10, and most desirably from about 6 to 9. Various buffers may be used to achieve and maintain the pH during the assay procedure. Representative buffers include borate, citrate, acetate, phosphate, carbonate, tris, barbital and the like. The particular buffer employed is not critical to the present invention, but the tris and phosphate buffers are preferred. The cation portion of the buffer will generally determine the cation portion of the tracer salt in solution.

Riboflavin binding protein (RBP) may be added to the sample or to one or more of the assay reagents in order to bind any riboflavin present in the sample into RBP riboflavin complexes, thus eliminating potential fluorescence interference from riboflavin. RBP is a protein of approximately 32,000 M.W. which is commonly isolated from egg whites. Upon isolation from the egg, each molecule of RBP contains one molecule of riboflavin. This, the holoprotein form of RBP, must be converted to the apoprotein form by dialysis, under acidic conditions, to remove the bound riboflavin. The RBP apoprotein utilized in the present invention is commercially available from Sigma Chemical Company, St. Louis, Mo. The amount used is not critical, provided a sufficient quantity is used to bind virtually all free riboflavin in the sample.

The preferred method of the improved assay of the present invention will now be discussed in detail. The assay is a "homogeneous assay", which means that the end polarization readings are taken from a solution in which bound tracer is not separated from unbound tracer. This represents a distinct advantage over heterogeneous immunoassay procedures wherein the bound tracer must be separated from the unbound tracer before a reading can be taken.

The reagents for the fluorescence polarization assay of the present invention comprise antibody selective for opiate alkaloids and their metabolites and tracer. Additionally, largely conventional solutions including an opiate alkaloid-specific pretreatment solution, a dilution buffer, opiate alkaloid calibrators and opiate alkaloid controls are desirably prepared. Typical solutions of these reagents, some of which are described herein, are commercially available in assay "kits" from Abbott Laboratories, Abbott Park, Ill.

All percentages expressed herein are weight/volume unless otherwise indicated. The tracer formulation presently preferred is 200 nanomolar tracer in: 0.1 molar citrate buffer at pH 6.0; 5% 5-sulfosalicylate; and 0.1% sodium azide. The antiserum formulation comprises sheep antiserum diluted with: 3.3% normal sheep serum (volume/volume); 0.1 M Tris buffer at pH 7.5, 2% ethylene glycol and 0.1% sodium azide. The dilution buffer comprises: 0.1 molar sodium phosphate at pH 7.5; 0.1% sodium azide; and 0.01% bovine gamma globulin. The pretreatment formulation comprises: 0.1 molar Tris buffer at pH 7.5; 4 mg/ml riboflavin binding protein; and 0.1% sodium azide. The wash solution is the same as the dilution buffer listed above. Calibrators comprising morphine alkaloid in normal human urine at concentrations of 0.0, 100, 200, 350, 600 and 1000 micrograms per liter, with 0.1% sodium azide preservative, are useful. Controls comprising morphine alkaloid in normal human urine are provided at concentrations of 250 and 800 micrograms per liter with 0.1% sodium azide as a preservative.

The preferred procedure is especially designed to be used in conjunction with the Abbott TDx® polarization analyzer available from Abbott Laboratories, Irving, Tex. 50 microliters of urine, serum or plasma are required. The calibrators, controls, or unknown samples are pipetted directly into the sample well of the TDx® sample cartridge. One of the advantages of this procedure is that the sample does not require any special preparation. If a TDx® opiate alkaloid assay kit is being used with the TDx® analyzer, samples are placed directly into a sample carousel, the caps from each of the four reagent containers in the kit are removed and placed into designated wells inside the TDx ® analyzer, and the assay procedure from this point is fully automated.

If a manual assay is being performed, the sample is mixed with the pretreatment solution in dilution buffer and a background reading is taken. The tracer is then mixed with the assay. The antibody is then finally mixed into the test solution. After incubation, a fluorescence polarization reading is taken.

The fluorescence polarization value of each calibrator, control or sample is determined and may be printed on the output tape of an instrument such as the Abbott TDx ® polarization analyzer. A standard curve is generated in the instrument by plotting the polarization of each calibrator versus its concentration using nonlinear regression analysis. The concentration of each control or sample is read off the stored calibration curve and printed on the output tape.

With respect to the foregoing preferred procedure, it should be noted that the tracer, antibody, pretreatment solution, calibrators and controls should be stored between about 2° and about 8° C., while the dilution buffer should be stored at ambient temperature. A standard curve and controls should be run every two weeks, with each calibrator and control run in duplicate. Controls should be run daily and all samples can be run in replicates if so desired.

It should be understood that the foregoing Detailed Description and the following Examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples 1 through 19 describe experiments that were performed in accordance with the concepts of the present invention.

EXAMPLE 1

Morphine-3-glucuronide Immunogen

Morphine 3-glucuronide (100.4 mg) was dissolved in 12 ml of distilled water with the addition of 3 drops of 1.0M NaOH. Sodium periodate (36 mg) was added, the pH was adjusted to 3, and the mixture was stirred at room temperature for 1½ hours. Ethylene glycol (0.016 ml) was added and stirring was continued for 1 hour. Thyroglobulin (50.6 mg) was added, the pH was adjusted to 8 and, after another hour, one equivalent of sodium cyanoborohydride was added. After stirring overnight, the solution was dialyzed against saline for two days.

EXAMPLE 2

Morphine 3 (ethoxy carbonylmethyl) Ether

Morphine (86 mg) was dissolved in 1.3 ml of absolute ethanol upon treatment with 0.345 ml of a 1.0 M solution of potassium ethoxide in ethanol. Ethyl bromoacetate (57.6 mg) was added, and the mixture was stirred at room temperature under nitrogen atmosphere for 7 hours. The product was purified by chromatography on a silica gel thick layer plate, developing with 2:1 chloroform; methanol, to give 39 mg of a clear glass.

EXAMPLE 3

7.8 Dihydromorphine 3-(ethoxycarbonylmethyl) Ether Hydrochloride)

Morphine 3-ethoxycarbonylmethyl ether (39 mg) was hydrogenated in 15 ml ethanol and 0.009 ml of concentrated hydrochloric acid over 10 mg of 10% palladium on carbon at an initial pressure of 40 psi. After 2 hours the product was isolated by filtration and removal of solvent to give 49 mg of a colorless glass.

EXAMPLE 4

7-8 Dihydromorphine 3 [(2 aminoethyl)amino carbonylmethyl] Ether Hydrochloride 7,8 Dihydromorphine-3-(ethoxycarbonylmethyl) ether (49 mg) was dissolved in 1.0 ml methanol and 0.20 ml of freshly distilled 1,2 diaminoethane was added. The mixture was allowed to stir at room temperature under nitrogen atmosphere for 16 hours. Thorough removal of volatile materials in vacuo left 58 mg of a clear glass, pure enough for conjugation to fluorescent label.

EXAMPLE 5

7,8-Dihydromorphine-3-{2-[4-(fluorescein-6ylamino)-6-chloro-1,3,5-triazin-2-ylamino]-ethylamino carbonylmethyl} Ether 7,8-Dihydromorphine-3-[(2-aminoethyl) amino-carbonylmethyl] ether hydrochloride (19 mg) was dissolved in 0.75 ml of methanol and 27.9 mg of dichlorotriazinylaminofluorescein (isomer II) was added. After stirring at room temperature for 30 hours, the mixture was diluted with 0.20 ml of dimethylformamide and streaked onto a thick-layer silica gel chromatography plate. Development with chloroform methanol-acetic acid gave the purified tracer.

EXAMPLE 6

7,8-Dihydromorphine-3-(ethoxycarbonylmethyl) Ether from 7,8-Dihydromorphine 7,8 Dihydromorphine (144 mg) and potassium tert-butoxide (67 mg) were dissolved by warming gently in 2.5 ml of dimethylformamide (dried over 3A molecular sieves). The solution was cooled, and 100 mg of ethyl bromoacetate was added. The mixture was stirred at room temperature under nitrogen atmosphere for 2½ hours, quenched by addition of 0.006 ml of glacial acetic acid, and taken to dryness on a rotary evaporator. The residue was chromatographed on a silica gel thick layer plate, developed with chloroform /methanol/acetic acid to give 170 mg of the acetate salt of the title compound.

EXAMPLE 7

7,8 Dihydromorphine-3 Carboxymethyl Ether

The acetate salt of 7,8 dihydromorphine-3-(ethoxycarbonylmethyl) ether (164 mg) was dissolved in 2 ml of methanol plus 2 ml of water and 1 ml of 2M aqueous sodium hydroxide was added. The solution was stirred at room temperature under nitrogen atmosphere for 5 hours. Solvents were removed on a rotary evaporator. The residue was taken up in 1 ml of 3M aqueous hydrochloric acid and again taken to dryness, to leave the product as its hydrochloride salt, admixed with sodium chloride, but otherwise essentially pure by thin-layer chromatography and NMR spectrum.

EXAMPLE 8

7,8-Dihydromorphine-3-(fluorescein-6-ylamino-carbonylmethyl) Ether 7,8-Dihydromorphine-3-carboxymethyl ether hydrochloride (0.1 mmol) was dissolved in 0.3 ml of dimethylformamide. The solution was cooled in an ice bath and 0.014 ml triethylamine and 0.0105 ml of ethyl chloroformate were added. The solution was stirred for 1½ hours, and half of it was allowed to react with 6-aminofluorescein at room temperature overnight. The product was purified by chromatography on a silica gel thin layer plate, developing with chloroform/methanol/acetic acid, then on a second plate developed with chloroform/methanol.

EXAMPLE 9

Morphine-3-ethoxycarbonylmethyl Ether-N-Oxide

Morphine-3-ethoxycarbonylmethyl ether (59 mg) was taken up in 0.5 ml of 30% hydrogen peroxide and heated in an oil bath at 70° C. for 20 minutes. Volatile materials were removed in vacuo to leave 62 mg of nearly pure product as a crystalline solid.

EXAMPLE 10

Morphine-3-carboxylmethyl Ether-N-Oxide Hydrochloride

Morphine-3-ethoxycarbonylmethyl ether-N-oxide (40 mg.) was dissolved in 1 ml of methanol plus 1 ml of water, and 0.25 ml of 2M aqueous sodium hydroxide was added. The mixture was stirred at room temperature overnight, and solvents were removed on a rotary evaporator. The residue was redissolved in 0.35 ml of 3M aqueous hydrochloric acid and again taken to dryness to give 72 mg of the title compound, with a calculated 29 mg of sodium chloride as the principal contaminant.

EXAMPLE 11

1-Chloromorphine-3-(3-aminopropyl) Ether Hydrochloride

Morphine-3-(3-azidopropyl) ether (46.5 mg.) was dissolved, under nitrogen, in 0.5 ml methanol and 50.5 mg of triethylamine was added, followed by 54 mg of 1,3-propanedithiol. The mixture was stirred for 16 hours at ambient temperature, filtered, an the filtrate was concentrated in vacuo. The residue was acidified with 6M hydrochloric acid and extracted with ether. The aqueous portion was concentrated to dryness in vacuo to yield the product. Subsequent testing of the ether employed in the extraction showed significant contamination with peroxides.

EXAMPLE 12

1-Chloromorphine-3-[3-(fluorescein-6-ylcarbonylamino) propyl] Ether

1-Chloromorphine-3-(3-aminopropyl) ether (6 mg) and 6.6 mg of 6 (N succinimidyloxycarbonyl) fluorescein in 0.3 ml of dry pyridine were stirred at ambient temperature for 22 hours. The reaction mixture was streaked directly onto a silica gel chromatography plate and dried in a vacuum oven. The plate was developed with chloroform/methanol and the band containing the desired conjugate was extracted with methanol.

EXAMPLE 13

7,8 Dihydromorphine 3-(2-aminoethyl) Ether

Morphine-3-(2-azidoethyl) ether (140 mg) and 30 mg of 10% palladium on carbon were taken up in ethanol and 3M hydrochloric acid and hydrogenated at 3 atmospheres pressure and ambient temperature for 16 hours. The reaction mixture was filtered, and the filtrate was concentrated to dryness on a rotary evaporator. The residue was chromatographed over silica gel with chloroform/methanol/ammonium hydroxide. The fractions containing primary amine were combined and concentrated in vacuo to yield the product.

EXAMPLE 14

7,8-Dihydromorphine-3-(2-[fluorescein-5-ylcarbonylamino] ethyl) Ether

5-Carboxyfluorescein (5.25 mg) and 2 mg N-hydroxysuccinimide were mixed in dimethylformamide (0.3 ml). Dicyclohexylcarbodiimide (2.2 mg) was added and the mixture stirred for two hours at ambient temperature. 7,8-Dihydromorphine-3-(2-aminoethyl) ether (5.3 mg) and 2.1 mg pyridine were added and this mixture stirred at ambient temperature for 48 hours. The reaction mixture was streaked onto a silica gel chromatographic plate and developed with chloroform/methanol to yield the desired conjugate.

EXAMPLE 15

7,8-Dihydromorphine-3-[2-(fluorescein-5-ylamino carbonylmethyleneamino)ethyl] Ether 7,8-Dihydromorphine-3-(2 aminoethyl) ether hydrochloride (5.3 mg) and 9.4 mg of 5-(bromoacetamido)-fluorescein were mixed in 0.3 ml of methanol plus 0.08 ml of dimethylformamide, and 9.7 mg of triethylamine was added. The reaction mixture was stirred for 16 hours at ambient temperature and chromatographed on a silica gel plate with chloroform/methanol/acetic acid to give the desired conjugate.

EXAMPLE 16

1-Chloromorphine-3-{3-[4-(fluorescein-5-ylamino)6-chloro-1,3,5-triazin-2-ylamino]propyl} Ether 1-Chloromorphine-3-(3-aminopropyl) ether 5.0 mg, 7.5 mg 5-(4,6-dichoro-1,3,5 triazin-2ylamino)fluorescein and 6.7 mg of triethylamine were stirred for 16 hours at ambient temperature in methanol. The reaction mixture was streaked onto a silica gel chromatography plate and developed with chloroform/methanol/acetic acid t give the desired conjugate.

EXAMPLE 17

1-Chloromorphine-3-{3-[4-(fluorescein-6-ylamino)-6-chloro-1,3,5-triazin--2-ylamino]prooyl} Ether This compound was prepared according to the method of Example 16 from 6.0 mg 1-chloromorphine -(3-aminopropyl) ether and 7.5 mg of 6-(4,6-dichloro-1,3,5-triazin-2-ylamino)fluorescein.

EXAMPLE 18

7,8-Dihydromorphine-3-{2-[4-(fluorescein-5-ylamino)-6-chloro-1,3,5-triazin-2-ylamino]ethyl} Ether This compound was prepared according to the method of Example 16 from 5.3 mg of 7,8-dihydromorphine-3-(2 aminoethyl) ether hydrochloride, 7.5 mg of 5-(4,6-dichloro-1,3,5-triazin-2-ylamino)fluorescein and 97 mg of triethylamine.

EXAMPLE 19

7,8-Dihydromorphine-3-{2-[4-(fluorescein-6-ylamino)--(6-chloro-1,3,5-triazin--2-ylamino]ethyl} Ether

This compound was prepared according to the method of Example 16 from 5.3 mg 7,8 dihydromorphine-3-(2-aminoethyl) ether hydrochloride, 7.5 mg 6-(4,6-dichloro-1,3,5-triazin-2-ylamino)fluorescein and 9.7 mg of triethylamine.

Figure 2:
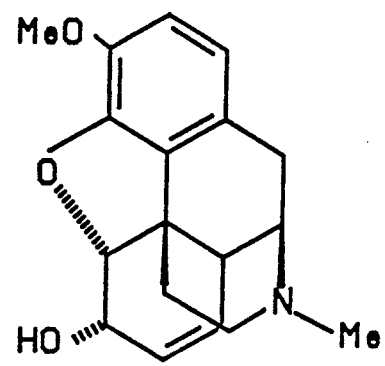
Figure 3:
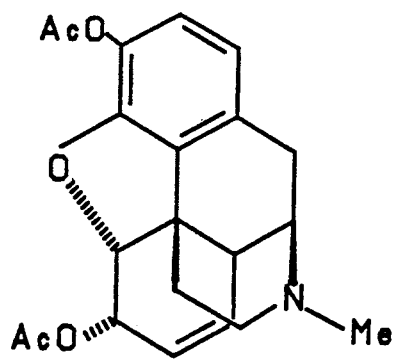
Figure 4:
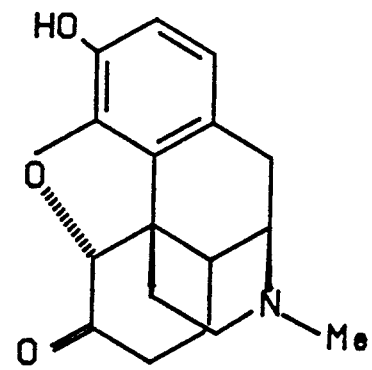
Figure 5:
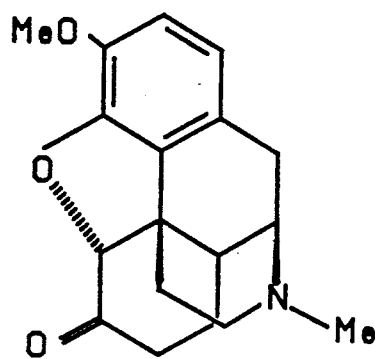
Figure 6:
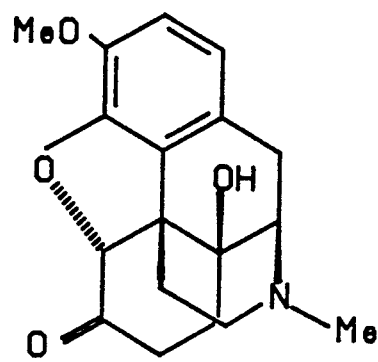
Figure 7:
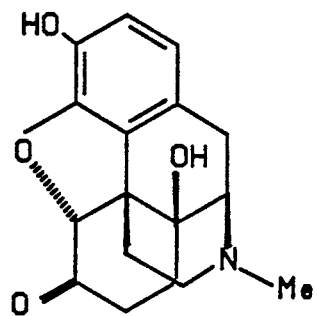
Figure 8:
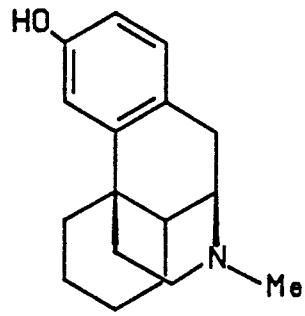
Figure 10:
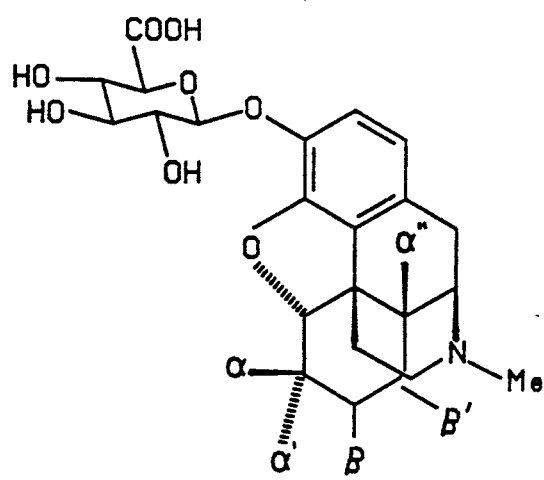
FIG. 10 shows a general structural formula for glucuronic acid conjugates of phenolic opiates which can serve as synthetic precursors for the haptens of the present invention.
Figure 12:
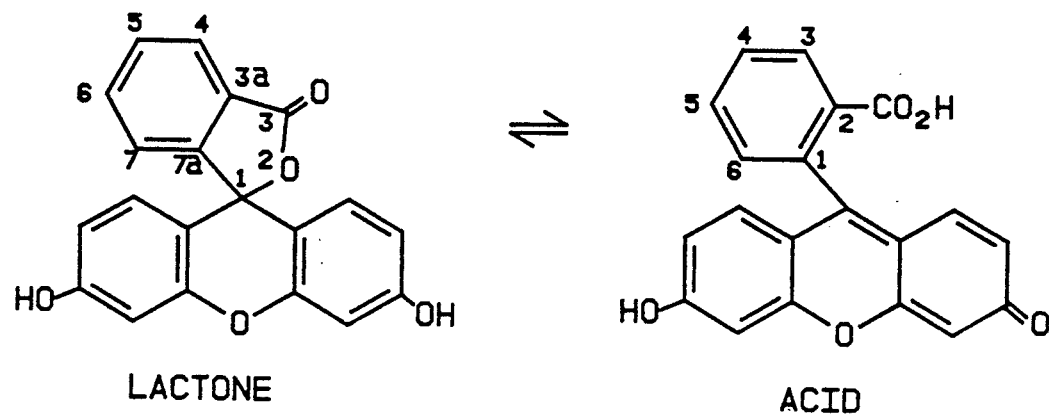
FIG. 12 shows the alternate structural formulae and names of the fluorescein moiety included in the tracers of the present invention.

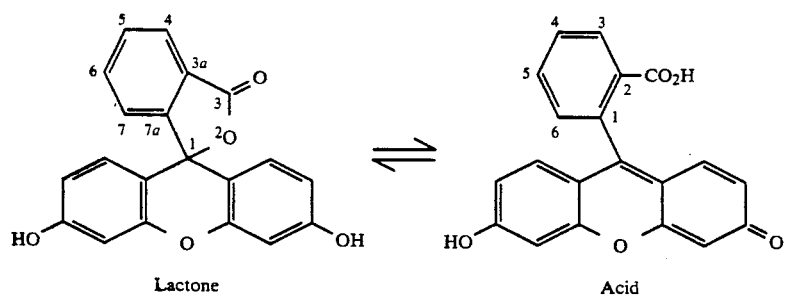
FIG. 12
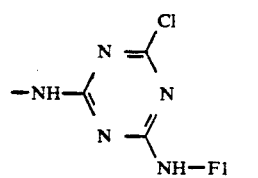
FIG. 13-1
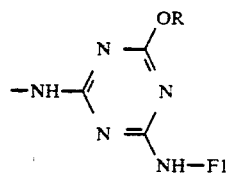
FIG. 13-2
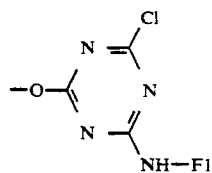
FIG. 13-3
—NH—CO—Fl    FIG. 13-4
—CO—NH—Fl    FIG. 13-5
—C(NH)—NH—Fl    FIG. 13-6
—NH—CO—NH—Fl    FIG. 13-7
—O—CO—NH—Fl    FIG. 13-8
—SO$_2$—NH—Fl    FIG. 13-9
—O—CO—NH—SO$_2$—NH—Fl    FIG. 13-10
FIG. 14
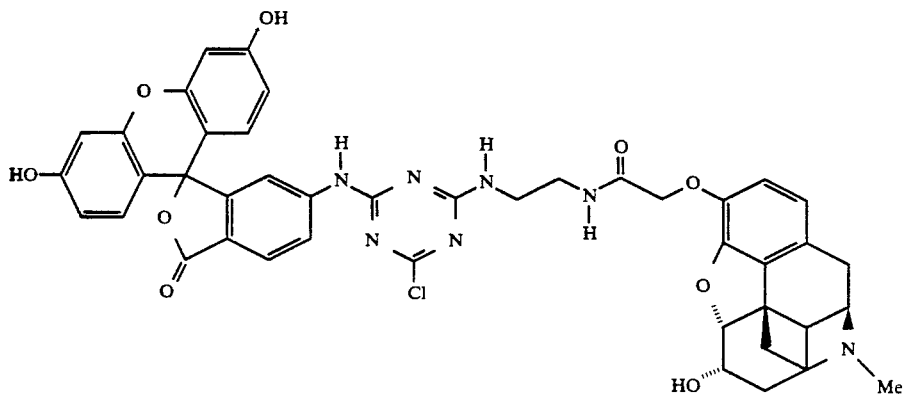

-continued

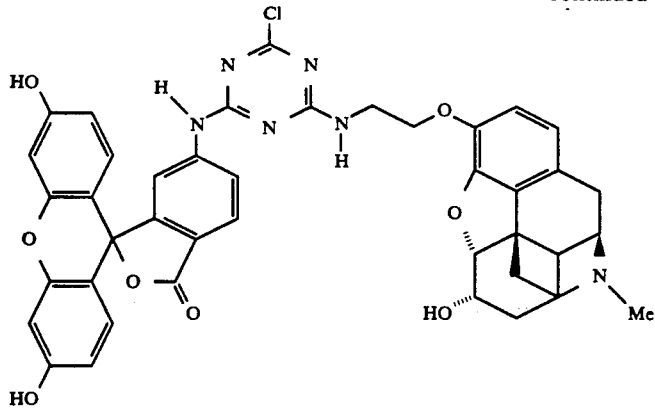

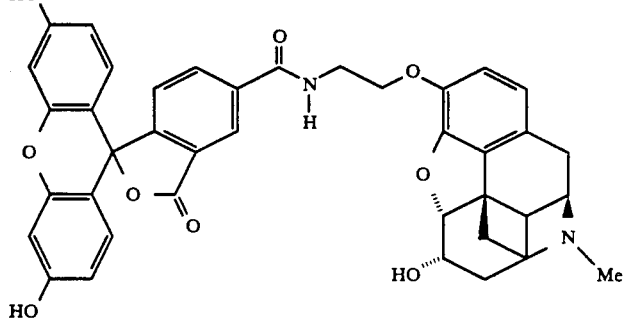

FIG.23

FIG. 24

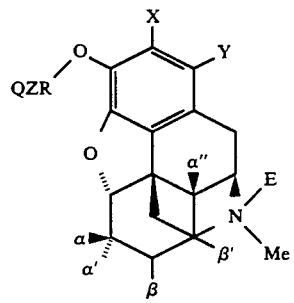

wherein:
one of X and Y is hydrogen and the other is hydrogen, fluorine, chlorine, bromine, cyano or $C_1$-$C_3$ alkyl;

Z is a linking functional group such as >NH, >>C=O, >SO$_2$ or —S—;

Q is hydrogen, hydroxyl or a leaving group;

R is a linking group consisting of from 0 to 20 carbon atoms and heteroatoms, including not more than 12 heteroatoms, the heteroatoms being N, O, S, Cl, I, or Br, arranged in a straight or branched chain and containing up to two rings structures, with the proviso that not more than four heteroatoms may be linked in sequence, nor may more than two sulfur or two nitrogen or one oxygen atom be linked in sequence;

E is a nonbonding electron pair, an oxygen atom or methyl;

$\alpha$ and $\alpha'$ are both hydrogen, or one of them is hydrogen while the other is hydroxyl, methyl or fluoro, or both are taken together to form =O (ketone);

$\alpha''$ is hydrogen or hydroxyl; and $\beta$ and $\beta'$ are both hydrogen, or both are taken together to form a bond joining the two carbon atoms to which they are attached, with the proviso that $\beta$ and $\beta'$ do not form a bond when $\alpha$ is H, $\alpha'$ is OH, E is an electron pair and $\alpha''$, X and Y are all hydrogen.

What is claimed is:
1. A compound comprising the structure:

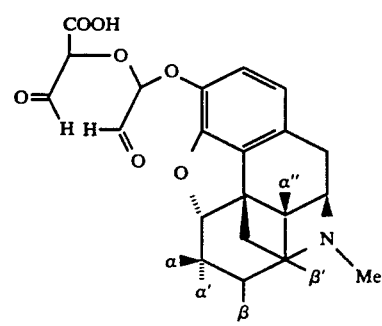

wherein one of $\alpha$ and $\alpha'$ is hydrogen and the other is hydroxyl, or both are taken together to form =O (ketone); $\beta$ and $\beta'$ are both hydrogen, or both are taken together to form a bond joining the carbon atoms to which they are attached; and $\alpha''$ is hydrogen or hydroxyl.

2. A compound comprising the structure:

* * * * *